United States Patent [19]

Mitnick

[11] Patent Number: 4,983,122
[45] Date of Patent: Jan. 8, 1991

[54] DENTAL COMPRESS

[76] Inventor: Neal I. Mitnick, 5118 14th Ave., Brooklyn, N.Y. 11219

[21] Appl. No.: 319,478

[22] Filed: Mar. 3, 1989

[51] Int. Cl.$^5$ .......................... A61C 19/06; A61F 7/12
[52] U.S. Cl. ...................................... 433/229; 128/401
[58] Field of Search ...................... 128/401, 403; 433/6, 433/32, 215, 229

[56] References Cited

U.S. PATENT DOCUMENTS

| | | | |
|---|---|---|---|
| 1,002,364 | 9/1911 | Bridges | 128/401 |
| 2,167,467 | 7/1939 | Sisson | 128/401 |
| 2,257,329 | 9/1941 | Britt | 433/215 |
| 2,429,238 | 10/1947 | Restarski et al. | 128/403 |
| 3,439,681 | 4/1969 | Riley | 128/401 |
| 3,780,537 | 12/1973 | Spencer | 62/530 |
| 3,840,992 | 10/1974 | English | 128/62 A |
| 3,848,607 | 11/1974 | St. Clair | 128/401 |
| 3,885,403 | 5/1975 | Spencer | 62/530 |
| 4,173,219 | 11/1979 | Lentine | 128/260 |
| 4,240,436 | 12/1980 | Singleton | 128/403 |
| 4,586,506 | 5/1986 | Nangle | 128/403 |

*Primary Examiner*—John J. Wilson
*Attorney, Agent, or Firm*—Rosen, Dainow & Jacobs

[57] ABSTRACT

A device for use as a hot or cold dental compress comprising a flexible, thermally non-conductive mouthpiece insertable in the upper or lower oral cavity is disclosed. One or more thermal bags comprising a temperature storage medium enclosed in flexible sealed envelopes are secured to the interior and/or exterior surfaces of the mouthpiece. The temperature storage medium comprises a non-toxic substance which maintains its gel-like consistency over a wide range of temperature. The thermal bags are heated or cooled and the compress used to treat affected areas of the mouth, cheeks, palate, gums or tongue. A method of treating affected areas of the oral cavity of a patient is also disclosed.

36 Claims, 3 Drawing Sheets

DENTAL COMPRESS

BACKGROUND OF THE INVENTION

This invention concerns a removable, disposable appliance or device for use as a thermal dental compress for the reduction of swelling and the relief of pain resulting from dental surgery or trauma to the mouth, palate, cheeks, gums or tongue. Specifically, this invention concerns a device suitable for insertion in the mouth for use as a cold or hot compress. Said device has a shape complementary to the configuration of the upper or lower oral cavity so as to readily conform thereto, for use during post-operative oral surgery and following trauma to the mouth. A method of treating affected areas of the oral cavity of a patient is also disclosed.

Typically, the preferred method of reducing swelling in the mouth area is the application of an ice or heat pack having water or some other liquid or solid substance as its temperature storage medium externally to the face, in the area adjacent the mouth, cheek or jaw.

The use of ice or heat packs is widespread and recognized for the effective treatment of pain and swelling caused by surgery or traumatic injury. The application of ice or heat to the affected area in the first 10 hours after surgery or injury reduces swelling and pressure at the injured site, thereby substantially reducing pain. Bleeding is also substantially minimized as capillary vessels are constricted by the application of a cold compress locally to the affected site.

At the present time, there is no dental compress which is applied internally to any one of the lingual, buccal, labial, palatal, gingival or mucosal tissues of the mouth following dental or oral surgery, trauma to or biopsy of the mouth, tongue, cheeks or gums. To reduce swelling in the mouth, the current practice is to apply a hot or cold compress externally to the face in the mouth, cheek or jaw region.

Cold or hot packs are generally comprised of a flexible envelope or enclosure enclosing a water or chemical slurry which serves as a temperature storage medium. For instance, U.S. Pat. Nos. 3,780,537 and 3,885,403 to Spencer disclose a device for use as a hot and cold compress comprising a tough, flexible, sealed envelope made of a transparent, thermoplastic film such as polyethylene containing a liquid or paste or gel which has a low freezing point and a high boiling point. Preferably, the liquid is a gel which maintains its gel-like consistency over a wide range of temperature nd is non-toxic and non-irritating even to an open wound. For use as a cold compress, the envelope containing the gel is put into a freezer or other chilling device for a short period of time; for use as a hot compress, the envelope containing the temperature storage medium is inserted in hot water or otherwise heated for a period of time.

SUMMARY AND OBJECTS OF THE INVENTION

Accordingly, it is an object of this invention to provide a removable, disposable appliance which has utility as a hot or cold compress for the reduction of swelling and the treatment of pain following dental or oral surgery, biopsy or other trauma to the mouth, palate, tongue, cheeks or gums.

It is another object of this invention to provide a compress which may be closely and comfortably applied to the internal aspects of the upper or lower oral cavities of the mouth;

It is a further object of this invention to provide a compress adapted to be inserted and retained in the mouth which protects the teeth and other uninvolved soft tissues from extremes of temperature and which is not easily aspirated.

Yet another object of the invention is to provide a method of treating affected areas of the oral cavity of a patient using a thermal compress.

It should be understood that while the present invention will find its most frequent use in dentistry, it is not limited in scope to dental applications. It is contemplated that the device of this invention may be used following trauma to the mouth regardless of cause, whether due to accidental injury, dental or plastic surgery, or biopsy of the mouth, tongue, cheeks or gums.

This invention comprises a device for use as a hot or cold dental compress. The compress comprises a sealed, flexible enclosure sized to be insertable into a mouth. Contained within the enclosure is a non-toxic temperature storage medium having a gel-like consistency over a wide temperature range. Means configured to be insertable into the mouth are provided for engaging the enclosure and for holding the enclosure against a surface in the mouth. Specifically, the compress of the invention comprises a flexible, thermally non-conductive mouthpiece which has an anatomical shape adapted to be inserted and retained in the mouth for treatment of swelling and other dysfunction of the oral cavity. The mouthpiece is available in two configurations to conform to the geometry of the upper and lower dental arch. Unlike prior art methods of treating pain and swelling of the oral cavity, e.g., applying cotton, guaze or ice to the affected area, which methods present a danger if the cotton, etc. is swallowed, the shape of the appliance of the present invention precludes aspiration of the compress. The compress is also advantageously disposable, eliminating the possibility of communicating infection or diseases.

In one embodiment of the device, the mouthpiece is insertable in the lower oral cavity and comprises a generally U-shaped base approximating and readily conforming to the curve of the lower dental arch. The base has an interior and an exterior rim and is positionable over the occlusal surfaces of the lower dentition. An integrally formed lingual flange, approximating and generally conforming to the lingual surfaces of the lower dentition and the gingival and mucosal surfaces of the lower oral cavity, extends downwardly from the interior rim of the base when the mouthpiece is positioned in the mouth. The lingual flange is generally greater in height at the end portions than at the middle portion of the U-shaped base of the mouthpiece to provide clearance for free movement of the tongue and to prevent patient gagging. One or more thermal bags comprising a temperature storage medium enclosed in a flexible sealed envelope are secured to the interior surface of the lingual flange of the mouthpiece so that the bags are in contact with at least one of the anterior or posterior lingual, gingival or mucosal surfaces of the lower oral cavity. Alternatively, one or more thermal bags may be secured to the exterior surface of the lingual flange of the mouthpiece, so as to contact and treat affected areas of the tongue.

In another embodiment of this invention, an integrally formed buccal flange may extend downwardly from the exterior rim of the base of the mouthpiece, said buccal flange approximating and generally conforming to the buccal and labial surfaces of the lower dentition and the gingival and mucosal surfaces of the lower oral cavity when the mouthpiece is positioned in the lower oral cavity. The buccal flange may take the place of the lingual flange or, alternatively, integrally formed lingual and buccal flanges may extend downwardly from the interior and exterior rims, respectively, of the base of the mouthpiece. Thermal bag(s) are secured to the interior and/or exterior surfaces of the buccal and lingual flanges of the mouthpiece, so that the bag(s) are in contact with at least one surface of the lower oral cavity.

In a further embodiment of the device, the mouthpiece is insertable in the upper oral cavity and comprises a generally U-shaped base approximating and readily conforming to the arch of the upper dentition. The base has an exterior and an interior rim and is positionable over the occlusal surfaces of the upper dentition. A palatal member comprising an integrally formed curved part approximating the shape of and readily conforming to the palate extends upwardly from the interior rim of the base. Thermal bag(s) are secured to the interior and/or exterior surfaces of the palatal member of the mouthpiece, so as to contact at least one of the palate, the palatal gingival surfaces, or the tongue.

In another embodiment of this invention, the mouthpiece is insertable in the upper oral cavity and comprises a generally U-shaped base approximating and readily conforming to the arch of the upper dentition. The base has an exterior and an interior rim and is positionable over the occlusal surfaces of the upper dentition. An integrally formed buccal flange, either alone or in combination with the palatal member, extends upwardly from the exterior rim of the base and approximates and generally conforms to the buccal and labial tooth surfaces and gingival and mucosal surfaces of the upper oral cavity when the mouthpiece is positioned in the upper oral cavity. Thermal bags are secured to the interior and/or exterior surfaces of the mouthpiece, so that the bags contact at least one surface of the upper oral cavity.

In any of these embodiments, the thermal bags may be secured directly to the base in those areas where teeth are absent, extracted, etc. Specifically, where a tooth has been removed from the alveolar ridge, a thermal bag(s) may be positioned on the rim of the base, directly over the extraction site.

DESCRIPTION OF THE DRAWINGS

Further objects and advantages of the invention will appear from the following description as well as from the accompanying drawings which illustrate certain embodiments of the invention. It will be understood that the invention is no limited to the embodiments described and that the drawings are for purposes of illustration only and are not intended as a definition of the limits of the invention. Similar reference numerals refer to similar elements throughout the several views.

DETAILED DESCRIPTION OF PREFERRED EMBODIMENTS

In a first embodiment of the hot or cold dental compress of this invention shown in FIGS. 1 through 4, the device comprises a flexible, thermally non-conductive mouthpiece 1 insertable in the upper oral cavity. The mouthpiece 1 has a first part comprising a generally U-shaped base 2 approximating and readily conforming to the arch of the upper dentition. The base 2 has an exterior rim 12 and an interior rim 13. The U-shaped base 2 is positionable by the user or the health care practitioner over the occlusal surfaces of the upper dentition. A palatal member 3 comprising an integrally formed curved part approximating the shape of and readily conforming to the palate extends upwardly from the base 2. The raised curved palatal member 3 is designed to complement the contour of the palate and to provide clearance for free movement of the tongue. A thermal bag 4 comprising a temperature storage medium enclosed in a flexible sealed envelope or enclosure is shown secured to the interior side surface of the palatal member 3 of the mouthpiece, so that the thermal bag 4 contacts the palate and the palatal gingival surfaces of the upper oral cavity. A second thermal bag 4 is shown in shadow in FIG. 1, secured to the front and central interior surface of the palatal member 3. Alternatively, thermal bag(s), not shown, may be secured to the exterior surface of the palatal member so as to contact the dorsal surface of the tongue.

A central slit 5 may optionally be provided in the palatal member 3 so that the palatal member comprises two flaps or halves 6 and 7. The two halves or flaps 6 and 7 of the palatal member 3 adjacent the central slit 5 may be overlapped or slid one over the other so as to narrow the size of the palatal member 3 and facilitate placement in the user's mouth. The user bites down on the base of the mouthpiece to hold it in place, illustrated by teeth 20 shown in FIGS. 2 and 3.

Thermal bags 4 may be positioned and secured anywhere on the interior and/or exterior surfaces of the palatal member 3 as indicated generally in FIGS. 1 through 4. Thermal bag(s) may also be placed directly on the base in those locations where teeth are absent.

Figure 11:
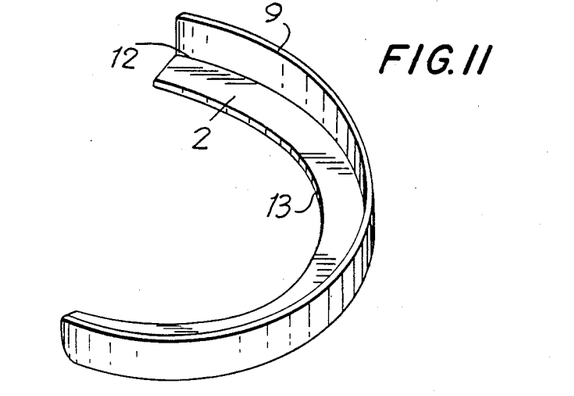
FIG. 11 is a perspective view of a further embodiment of the device of this invention, having an integrally formed buccal flange extending upwardly from the exterior rim of the base of the mouthpiece.

In another embodiment of this invention, illustrated in FIG. 11, the device comprises a flexible, thermally non-conductive mouthpiece 1 insertable in the upper oral cavity. The mouthpiece has a first part comprising a generally U-shaped base 2 approximating and readily conforming to the arch of the upper dentition. The base has an exterior rim 12 and an interior rim 13 and is positionable by the practitioner or patient over the occlusal surfaces of the upper dentition. An integrally formed buccal flange 9 extends upwardly from the exterior rim 12 of the base 2, said buccal flange 9 approximating and generally conforming to the buccal and labial surfaces of the upper dentition and the gingival and mucosal surfaces of the upper oral cavity when the mouthpiece is positioned in the upper oral cavity. Thermal bags may be secured to the exterior and/or interior surfaces of the buccal flange. The thermal bag will contact at least one of the buccal, labial, gingival or mucosal surfaces of the upper oral cavity when the thermal bag is secured to the interior surface of the buccal flange and will contact the cheek when secured to the exterior surface of the buccal flange of the mouthpiece.

Figure 10:
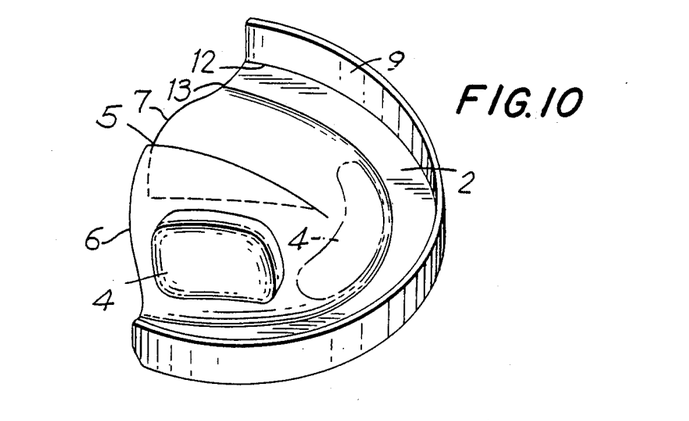
FIG. 10 is a perspective view of another embodiment of the device of this invention.

In yet another embodiment of this invention, shown in FIG. 10, the device comprises a flexible, thermally non-conductive mouthpiece insertable in the upper oral cavity. The mouthpiece has a first part comprising a generally U-shaped base 2 approximating and readily conforming to the arch of the upper dentition. The base 2 has an exterior rim 12 and an interior rim 13 and is positionable over the occlusal surfaces of the upper dentition. An integrally formed buccal flange 9 extends upwardly from the exterior rim 12 of the base 2, said buccal flange 9 approximating and generally conforming to the buccal and labial surfaces of the upper dentition and the gingival and mucosal surfaces of the upper oral cavity when the mouthpiece is positioned in the upper oral cavity. A palatal member 3 comprising a second integrally formed curved part approximating the shape of and readily conforming to the palate extends upwardly from the interior rim 13 of the base 2. Thermal bag(s) 4 may be secured to the interior and/or exterior surfaces of the palatal member 3 of the mouthpiece 1. The thermal bags may contact at least one of the palatal or palatal gingival surfaces of the upper oral cavity when the thermal bags are secured to the interior surface of the palatal member of the mouthpiece, and may contact the tongue when secured to the exterior surface of the palatal member of the mouthpiece. Thermal bags may also contact at least one of the buccal, labial, gingival or mucosal surfaces of the upper oral cavity when said bags are secured to the interior surface of the buccal flange of the mouthpiece, and may contact the cheek when secured to the exterior surface of the buccal flange of the mouthpiece.

In these latter two embodiments, the buccal flange is generally uniform in height, and ranges from 10 mm. to 30 mm., with the average height being about 25 mm. The buccal flange is easily trimmed with a pair of scissors at the frenula and/or tuberosity area of the second and third upper molar region to free mandibular movement and assure a comfortable fit in the patient's mouth.

Figure 1:
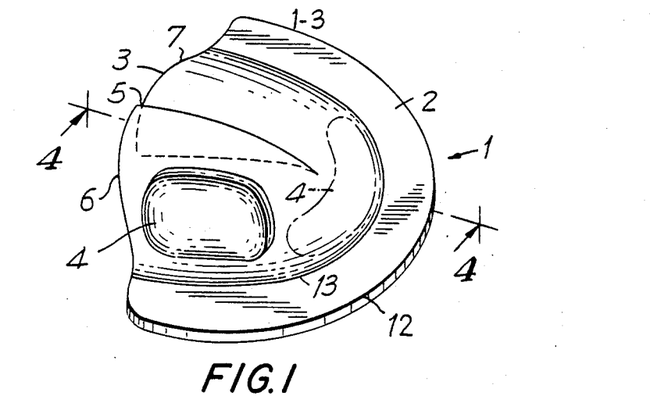
FIG. 1 is a perspective top view of one embodiment of the device of this invention.
Figure 2:
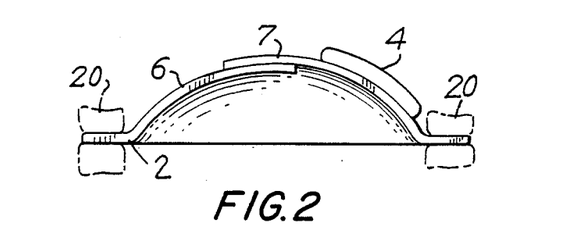
FIG. 2 is a side view of the embodiment of FIG. 1, showing a thermal bag positioned and secured to the right external surface of the palatal member.
Figure 3:
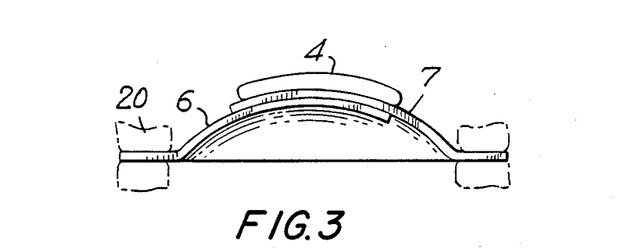
FIG. 3 is a side view of the embodiment of FIG. 1, showing a thermal bag positioned and secured to the central external surface of the palatal member.
Figure 4:
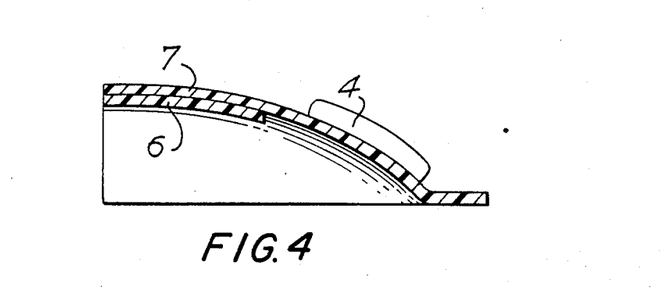
FIG. 4. is a cross-sectional view taken along lines 4—4 of FIG. 1.
Figures 5, 6:
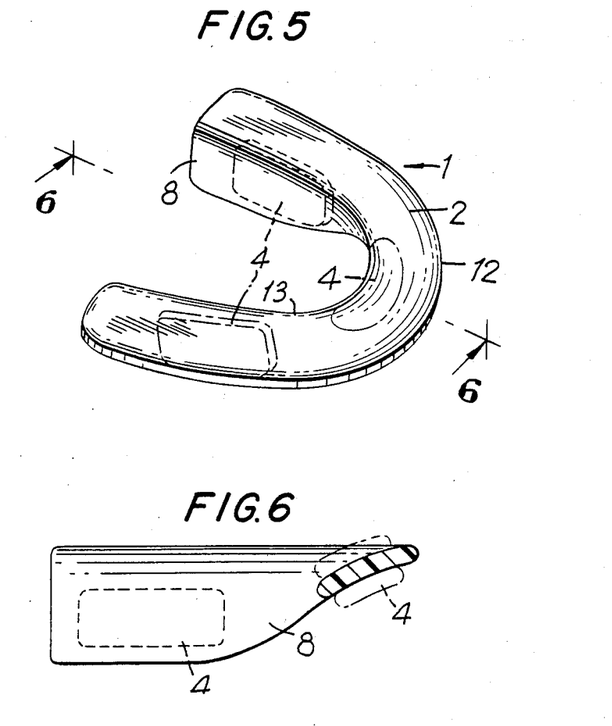
FIG. 5 is a perspective top view of a second embodiment of the device of this invention showing a thermal bag secured to the central internal surface of the lingual flange and additional thermal bags shown in shadow secured to the right and left internal surfaces of the lingual flange.
FIG. 6 is a sectional view taken along lines 6—6 of FIG. 5.
Figures 7, 8, 9:
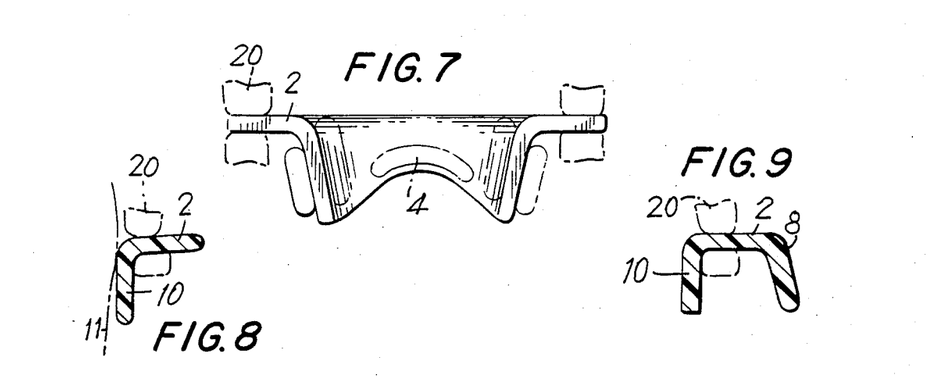
FIG. 7 is a rear view of the embodiment of FIG. 5;.
FIG. 8 is a sectional view of a further embodiment of the device of this invention, having an integrally formed buccal flange extending downwardly from the exterior rim of the base of the mouthpiece.
FIG. 9 is a sectional view of another embodiment of the device of this invention, having integrally formed buccal and lingual flanges extending downwardly from the exterior and interior rims of the base of the mouthpiece.

In a further embodiment of the invention, indicated in FIGS. 5 through 7, the device is adapted to be inserted in the lower oral cavity for the treatment of swelling and pain in the lower mouth region. The compress comprises a flexible, thermally non-conductive mouthpiece 1 insertable in the lower oral cavity comprising a generally U-shaped base 2 approximating and readily conforming to the curve of the lower dental arch. The base has an exterior rim 12 and an interior rim 13 and is configured to be positioned over the occlusal surfaces of the lower dentition. An integrally formed lingual flange 8 extends downwardly from the interior rim 13 of the base 2 when the mouthpiece 1 is positioned in the mouth. The lingual flange 8 is greater in height at the end portions than at the middle portion of the U-shaped base 2 and approximates and generally conforms to the lingual surfaces of the lower dentition and the gingival and mucosal surfaces of the lower oral cavity. The lingual flange 8 generally is from 5 mm. to 20 mm. in height at the middle portion of the base and from 5 mm. to 30 mm. in height at the end portions of the base, and generally measures about 25 mm. in height. The height of the flange may easily be adjusted by the user or the caregiver by trimming with scissors, so as to optimize fit in the user's mouth.

A thermal bag 4 is secured to the anterior central portion of the interior surface of the lingual flange 8 of the mouthpiece 1, as shown in FIG. 5. Additional thermal bags 4 are shown in shadow in FIGS. 5 through 7, said thermal bags positioned on the interior side surfaces of the lingual flange 8. The thermal bag(s) 4 are secured to the interior and/or exterior surfaces of the lingual flange 8 of the mouthpiece 1 so as to achieve direct contact with at least one of the anterior or posterior lingual, gingival or mucosal surfaces of the lower oral cavity when said bag is secured to the interior surface of the lingual flange and with the tongue when the thermal bag is secured to the exterior surface of the lingual flange of the mouthpiece, to reduce swelling and relieve pain as needed.

In a further embodiment of this invention shown in FIG. 8, the mouthpiece 1 comprises a generally U-shaped base 2 approximating and readily conforming to the curve of the lower dental arch. The base 2 has an exterior rim 12 and an interior rim 13 and is positionable over the occlusal surfaces of the lower dentition. However, in this embodiment, an integrally formed buccal flange 10 approximating and generally conforming to the buccal and labial surfaces of the lower dentition and the gingival and mucosal surfaces of the lower oral cavity extends downwardly from the exterior rim 12 of the base 2 when the mouthpiece 1 is positioned in the lower oral cavity. The buccal flange 10, shown in contact with cheek surface 11 in FIG. 8, is generally uniform in height, and ranges from 10 mm. to 30 mm. The average height of the buccal flange is about 25 mm.; however, the practitioner or patient may readily adjust the flange height to assure a comfortable fit by trimming the flange with scissors. One or more thermal bags are secured to the interior and/or exterior surfaces of the buccal flange 10 of the mouthpiece 1. The thermal bag may contact at least one of the anterior or posterior buccal, labial, gingival or mucosal surfaces of the mouth when the bag is secured to the interior surface of the buccal flange of the mouthpiece and may contact the cheek when secured to the exterior surface of the buccal flange of the mouthpiece.

Alternatively, integrally formed lingual and buccal flanges 8, 10 extend downwardly from the interior rims and exterior rims 13, 12 respectively, of the base 2 of the mouthpiece 1, as indicated in sectional view in FIG. 9. The buccal flange 10 approximates and generally conforms to the buccal and labial surfaces of the lower dentition and the gingival and mucosal surfaces of the lower oral cavity when the mouthpiece is positioned in the lower oral cavity, and the lingual flange 8 approximates and generally conforms to the lingual surfaces of the lower dentition and the gingival and mucosal surfaces of the lower oral cavity when the mouthpiece is positioned in the lower oral cavity. The lingual flange 8 is generally greater in height at the end portions than at the middle portion of the U-shaped base 2, to avoid patient discomfort and to assure retention in the mouth, whereas the buccal flange 10 is generally uniform in height, as stated above. One or more thermal bags 4 are secured to the interior and/or exterior surfaces of the buccal and lingual flanges 10, 8 of the mouthpiece 1. The thermal bags contact at least one of the anterior and/or posterior lingual, gingival or mucosal surfaces of the lower oral cavity when the bags are secured to the interior surface of the lingual flange of the mouthpiece and with the tongue when said bags are secured to the exterior surface of the lingual flange of the mouthpiece. The thermal bags may also contact at least one of the buccal, labial, gingival or mucosal surfaces of the mouth when secured to the interior surface of the buccal flange and with the cheek when secured to the exterior surface of the buccal flange of the mouthpiece.

Figure 12:
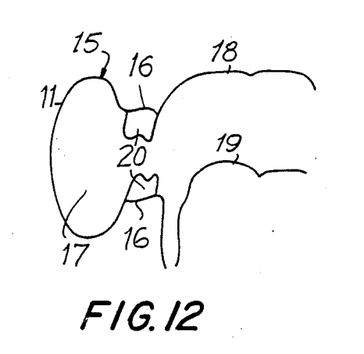
FIG. 12 is a schematic view of the oral cavity.
Figure 13:
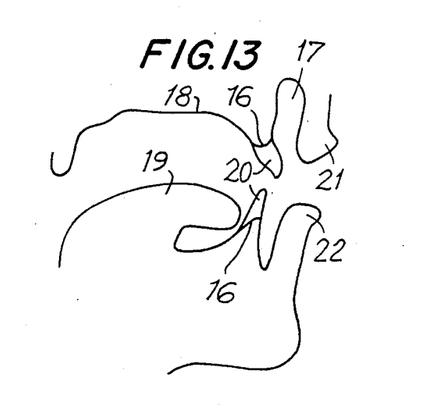
FIG. 13 is a schematic view of the face and oral cavity.

A compress according to this invention may optionally be placed on the mucobuccal fold 15 of the mouth, at the junction of the cheek 11 and the alveolar ridge 16 holding the teeth 20, illustrated schematically in FIGS. 12 and 13. Alternatively, thermal bag(s) may be positioned so as to apply cold or heat anywhere within the oral cavity and the vestibule 17, i.e., the space or potential space between the alveolar ridge 16 and the cheeks 11 and upper and lower lips, 21 and 22, respectively. The alveolar ridge 16 is shown adjacent the hard palate 18 and tongue 19 in FIGS. 12 and 13.

Thermal bags 4 are secured to the mouthpiece 1 by chemical or physical means, i.e. by means of adhesive or velcro, etc. applied to the bag for attaching the bag to the mouthpiece. It is contemplated that the device with thermal bags attached in various positions be available to dentists, pharmacists, physicians and hospitals preassembled. Alternatively, a supply of mouthpieces in three or more sizes to fit various sized upper and lower oral cavities and a supply of interchangeable and replaceable thermal bags in a variety of shapes and sizes be available for selection and assembly by the care-giver or the patient for localized treatment of the traumatized area. The thermal bags are positioned in and secured to the mouthpiece as necessary, in proper relation to and in contact with the areas to be treated.

In accordance with this invention, the mouthpiece may be made from any material which is sufficiently flexible to adapt to the shape of the mouth and yet sufficiently rigid to retain its shape in a heat or cold transferring relationship. A material such as styrofoam reinforced with fibers, such as is commonly used in face masks for its temperature-resistant properties, and which is waterproof, strong, and easily shaped is suitable for use in the compress of this invention. The mouthpiece advantageously is made from a material which readily bends inwardly or outwardly. Thus, the mouthpiece is designed to permit bending to conform the mouthpiece to the position most comfortable to the user so as to optimally treat affected areas of the mouth.

The mouthpiece shields sensitive structures such as the teeth and other soft uninvolved tissue from direct contact with extremes in temperature, and serves as the supporting structure for the thermal bag(s) in the mouth. It is contemplated that the mouthpiece be available in three sizes, in addition to pediatric sizes, to accommodate use by a variety of patients. To avoid patient discomfort and gagging, the mouthpiece is designed not to protrude into the soft palate or faucal pillars or against the posterior-most portion of the tongue when in use. When made of fiber-reinforced styrofoam, a typical thickness of the mouthpiece material would be between about 1.5 mm. to 3 mm. The critical considerations are that the mouthpiece must be thick enough to provide thermal insulation for temperature sensitive areas of the mouth, yet not be too bulky.

The thermal bag is constructed of a flexible plastic envelope or packet containing a temperature storage medium which contains a non-toxic substance, such as is disclosed in U.S. Pat. Nos. 3,780,537 and 3,885,403 to Spencer, which maintains its gellike consistency over a wide range of temperature. The thermal bag may be entirely or partially covered with a thin layer of gauze or other soft-surfaced, sterile material; such a material is more comfortable to the user than the plastic envelope of the thermal bag when in contact with the affected area. The gauze layer may be supplied attached to the surface of the thermal bag so as to contact the site to be treated or alternatively, may be applied by the user to the bag in the position desired. It is contemplated that the thermal bags will be available in a variety of shapes and sizes to conform to a portion or operative area of the user's mouth to which it is to be applied. The user or caregiver rapidly selects the desired shape and size thermal bag, positions it in the mouthpiece and secures or fastens it to the desired location by means of adhesive, velcro, etc. so that a snug fit is achieved against the oral tissues, tongue, cheeks or gums.

While a number of embodiments of the present invention have been shown and described, it will be obvious to one skilled in the art that many changes and modifications may be made thereto without departing from the spirit and scope of the invention.

I claim:

1. A device for use as a hot or cold compress, comprising:
    a sealed, flexible enclosure sized to be insertable into a mouth;
    a non-toxic temperature storage medium contained within said enclosure, said storage medium having a gel-like consistency over a wide temperature range; and
    means for engaging said enclosure and for holding said enclosure against a surface in the mouth, said means being configured to be insertable into the mouth and not to be easily aspirated.

2. A device for use as a hot or cold compress, comprising:
    a sealed, flexible enclosure sized to be insertable into a mouth;
    a non-toxic temperature storage medium contained within said enclosure, said storage medium having a gel-like consistency over a wide temperature range; and means for engaging said enclosure and for holding said enclosure against a surface in the lower oral cavity of the mouth, said means being configured to be inserted and retained in said lower oral cavity and not to be easily aspirated.

3. A device for use as a hot or cold compress, comprising:
   a sealed, flexible enclosure sized to be insertable into a mouth;
   a non-toxic temperature storage medium contained within said enclosure, said storage medium having a gel-like consistency over a wide temperature range; and
   means for engaging said enclosure and for holding said enclosure against a surface in the upper oral cavity of the mouth, said means being configured to be inserted and retained in said upper oral cavity and not to be easily aspirated.

4. A device for use as a hot or cold dental compress comprising:
   a mouthpiece insertable in the lower oral cavity comprising a generally U-shaped base approximating and readily conforming to the curve of the lower dental arch, said base having an exterior and an interior rim, said base being configured to be positionable over the occlusal surfaces of the lower dentition, an integrally formed lingual flange extending downwardly from the interior rim of said base when said mouthpiece is positioned in the mouth, said lingual flange approximating and generally conforming to the lingual surfaces of the lower dentition and the gingival and mucosal surfaces of the lower oral cavity when said mouthpiece is positioned in the lower oral cavity, said lingual flange being greater in height at the end portions than at the middle portion of said U-shaped base;
   a thermal bag comprising a temperature storage medium enclosed in a flexible sealed envelope, said temperature storage medium comprising a non-toxic substance which will maintain its gel-like consistency over a wide temperature range; and
   means for engaging and securing said thermal bag to the interior or exterior surface of said lingual flange of said mouthpiece.

5. A device according to claim 4 wherein said thermal bag is in contact with at least one of the anterior or posterior lingual, gingival or mucosal surfaces of the lower oral cavity when said thermal bag is secured to the interior surface of said lingual flange of said mouthpiece and wherein said thermal bag is in contact with the tongue when said thermal bag is secured to the exterior surface of said lingual flange of said mouthpiece.

6. A device according to claim 4 comprising a plurality of said thermal bags secured to said mouthpiece.

7. A device according to claim 4 wherein said mouthpiece is thermally non-conductive.

8. A device according to claim 4 wherein said lingual flange is from 5 mm. to 20 mm. in height at the middle portion of said base and from 5 mm. to 30 mm. in height at the end portions of said base.

9. A device according to claim 4 wherein said means for securing said thermal bag comprises adhesive applied to said bag for attaching said bag to said mouthpiece.

10. A device for use as hot or cold dental compress comprising:
    a mouthpiece insertable in the lower oral cavity comprising a generally U-shaped base approximating and readily conforming to the curve of the lower dental arch, said base having an exterior and an interior rim and being configured to be positionable over the occlusal surfaces of the lower dentition, an integrally formed buccal flange extending downwardly from the exterior rim of said base, said buccal flange approximating and generally conforming to the buccal and labial surfaces of the lower dentition and the gingival and mucosal surfaces of the lower oral cavity when said mouthpiece is positioned in the lower oral cavity, said buccal flange being generally uniform in height;
    a thermal bag comprising a temperature storage medium enclosed in a flexible sealed envelope, said temperature storage medium comprising a non-toxic substance which will maintain its gel-like consistency over a wide range of temperature; and
    means for engaging and securing said thermal bag to the interior or exterior surface of said buccal flange of said mouthpiece.

11. A device according to claim 10 wherein said thermal bag is in contact with at least one of the anterior or posterior buccal, labial, gingival or mucosal surfaces of the mouth when said thermal bag is secured to the interior surface of said buccal flange of said mouthpiece and wherein said thermal bag is in contact with the cheek when said thermal bag is secured to the exterior surface of said buccal flange of said mouthpiece.

12. A device according to claim 10 comprising a plurality of said thermal bags secured to said mouthpiece.

13. A device according to claim 10 wherein said buccal flange ranges from 10 mm. to 30 mm. in height.

14. A device according to claim 10 wherein said mouthpiece is thermally non-conductive.

15. A device for use as a hot or cold dental compress comprising:
    a mouthpiece insertable in the lower oral cavity comprising a generally U-shaped base approximating and readily conforming to the curve of the lower dental arch, said base having an exterior rim and an interior rim and being configured to be positionable over the occlusal surfaces of the lower dentition, integrally formed buccal and lingual flanges extending downwardly from the exterior and interior rims, respectively, of said base, said buccal flange approximating and generally conforming to the buccal and labial surfaces of the lower dentition and the gingival and mucosal surfaces of the lower oral cavity when said mouthpiece is positioned in the lower oral cavity, and said lingual flange approximating and generally conforming to the lingual surfaces of the lower dentition and the gingival and mucosal surfaces of the lower oral cavity when said mouthpiece is positioned in the mouth, said buccal flange being generally uniform in height and said lingual flange being greater in height at the end portions than at the middle portion of said U-shaped base:
    a plurality of thermal bags comprising a temperature storage medium enclosed in a flexible sealed envelope, said temperature storage medium comprising a non-toxic substance which will maintain its gel-like consistency over a wide range of temperature; and means for securing said thermal bags to at least one of the interior or exterior surfaces of said buccal and lingual flanges of said mouthpiece.

16. A device according to claim 15 wherein said bags are in contact with at least one of the lingual, gingival or mucosal surfaces of the lower oral cavity when said thermal bags are secured to the interior surface of said lingual flange of said mouthpiece and with the tongue when said bags are secured to the exterior surface of said lingual flange of said mouthpiece, and wherein said thermal bags are in contact with at least one of the buccal, labial, gingival or mucosal surfaces of the mouth when said thermal bags are secured to the interior surface of said buccal flange of said mouthpiece and with the cheek when said thermal bags are secured to the exterior surface of said buccal flange of said mouthpiece.

17. The device of claim 15 wherein said lingual flange is from 5 mm. to 20 mm. in height at the middle portion of said base and from 5 mm. to 30 mm. in height at the end portions of said base and wherein said buccal flange is generally uniform in height, and ranges from 10 mm. to 30 mm. in height.

18. A device according to claim 15 for use in a patient's mouth, including the vestibule, wherein said thermal bag is positioned and secured in said mouthpiece so as to contact the vestibule of the mouth.

19. A device according to claim 15 for use in a patient's mouth, including the mucobuccal fold, wherein said thermal bag is positioned and secured in said mouthpiece so as to contact the mucobuccal fold.

20. A device according to claim 15 wherein said mouthpiece is thermally non-conductive.

21. A device for use as a hot or cold dental compress comprising:
    a mouthpiece insertable in the upper oral cavity having a first part comprising a generally U-shaped base approximating and readily conforming to the arch of the upper dentition, said base having an exterior and an interior rim and being configured to be positionable over the occlusal surfaces of the upper dentition, and a palatal member comprising a second integrally formed curved part approximating the shape of and readily conforming to the palate and the palatal gingival surfaces of the upper oral cavity when said mouthpiece is positioned in the upper oral cavity of the mouth, said palatal member extending upwardly from the interior rim of said base;
    a thermal bag comprising a temperature storage medium enclosed in a flexible sealed envelope, said temperature storage medium comprising a nontoxic substance which will maintain its gel-like consistency over a wide range of temperature; and
    means for engaging and securing said thermal bag to the interior or exterior surface of said palatal member of said mouthpiece.

22. A device according to claim 21 wherein said thermal bag is in contact with at least one of the palatal or palatal gingival surfaces of the upper oral cavity when said thermal bag is secured to the interior surface of said palatal member of said mouthpiece and wherein said thermal bag is in contact with the tongue when said bag is secured to the exterior surface of said palatal member of said mouthpiece.

23. The device of claim 21 wherein a central slit is provided in said palatal member so that said palatal member comprises two flaps whereby one flap of the palatal member may be slid over the other so as to adjust the size of said mouthpiece to fit a variety of palates.

24. A device according to claim 21 comprising a plurality of said thermal bags secured to the interior and exterior surfaces of said palatal member of said mouthpiece.

25. A device according to claim 21 wherein said mouthpiece is thermally non-conductive.

26. A device for use as a hot or cold dental compress comprising:
    a mouthpiece insertable in the upper oral cavity having a first part comprising a generally U-shaped base approximating and readily conforming to the arch of the upper dentition, said base having an exterior and an interior rim, said base being configured to be positionable over the occlusal surfaces of the upper dentition, and an integrally formed buccal flange extending upwardly from the exterior rim of said bases said buccal flange approximating and generally conforming to the buccal and labial surfaces of the upper dentition and the gingival and mucosal surfaces of the upper oral cavity when said mouthpiece is positioned in the upper oral cavity, said buccal flange being generally uniform in height;
    a thermal bag comprising a temperature storage medium enclosed in a flexible sealed envelope, said temperature storage medium comprising a nontoxic substance which will maintain its gel-like consistency over a wide range of temperature; and
    means for engaging and securing said thermal bag to the interior or exterior surface of said buccal flange of said mouthpiece.

27. A device according to claim 26 wherein said bag is in contact with at least one of the buccal, labial, gingival or mucosal surfaces of the upper oral cavity when said thermal bag is secured to the interior surface of said buccal flange of said mouth piece and wherein said thermal bag is in contact with the cheek when said thermal bag is secured to the exterior surface of said buccal flange of said mouthpiece.

28. A device according to claim 26 comprising a plurality of said thermal bags secured to said mouthpiece.

29. A device according to claim 26 wherein said buccal flange ranges from 10 mm. to 30 mm. in height.

30. A device according to claim 26 wherein said mouthpiece is thermally non-conductive.

31. A device for use as a hot or cold dental compress comprising:
    a mouthpiece insertable in the upper oral cavity having a first part comprising a generally U-shaped base approximating and readily conforming to the arch of the upper dentition, said U-shaped base having an exterior and an interior rim, said base being configured to be positionable over the occlusal surfaces of the upper dentition, an integrally formed buccal flange extending upwardly from the exterior rim of said base, said buccal flange approximating and generally conforming to the buccal and labial surfaces of the upper dentition and the gingival and mucosal surfaces of the upper oral cavity when said mouthpiece is positioned in the upper oral cavity of the mouth, said buccal flange being generally uniform in height; and a palatal member comprising a second integrally formed curved part approximating the shape of and readily conforming to the palate and the palatal gingival surfaces of the upper oral cavity when said mouthpiece is positioned in the upper oral cavity of the mouth, said palatal member extending upwardly from the interior rim of said base;

a plurality of thermal bags comprising a temperature storage medium enclosed in flexible sealed envelopes, said temperature storage medium comprising a non-toxic substance which will maintain its gel-like consistency over a wide range of temperature; and means for engaging and securing said thermal bags to at least one of the interior or exterior surfaces of said buccal flange and palatal member of said mouthpiece.

32. A device according to claim 31 wherein said bags are in contact with at least one of the palatal or palatal gingival surfaces of the upper oral cavity when said thermal bags are secured to the interior surface of said palatal member of said mouthpiece and with the tongue when said bags are secured to the exterior surface of said palatal member of said mouthpiece and wherein said bags are in contact with at least one of the buccal, labial, gingival or mucosal surfaces of the upper oral cavity when said thermal bags are secured to the interior surface of said buccal flange of said mouthpiece and with the cheek when said thermal bags are secured to the exterior surface of said buccal flange of said mouthpiece.

33. The device of claim 31 wherein a central slit is provided in said palatal member so that said palatal member comprises two flaps whereby one flap of the palatal member may be slid over the other so as to adjust the size of said mouthpiece to fit a variety of palates.

34. A device according to claim 31 wherein said mouthpiece is thermally non-conductive.

35. A method of treating affected areas of the oral cavity of a patient, comprising providing a mouthpiece configured to be engaged by the upper or lower dental arch; said mouthpiece having associated therewith in a sealed enclosure a non-toxic temperature storage medium which is gel-like over a wide temperature range and which is positioned to contact the affected area when said mouthpiece is inserted in said oral cavity; heating or cooling said temperature storage medium; and inserting said mouthpiece into the patient's oral cavity and engaging it with the patient's upper or lower dental arch.

36. The method of claim 35 wherein said mouthpiece shields the teeth from said heated or cooled temperature storage medium.

* * * * *